(12) United States Patent
Greenfield et al.

(10) Patent No.: US 6,808,927 B2
(45) Date of Patent: Oct. 26, 2004

(54) METHOD OF PREPARATION OF STABILIZED THROMBIN-ACTIVATABLE FIBRINOLYSIS INHIBITOR (TAFI) AND METHODS OF USE THEREOF

(75) Inventors: Robert S. Greenfield, Trumbull, CT (US); Seong Soo A. An, Hopewell Junction, NY (US)

(73) Assignee: American Diagnostica, Inc., Stanford, CT (US)

( * ) Notice: Subject to any disclaimer, the term of this patent is extended or adjusted under 35 U.S.C. 154(b) by 96 days.

(21) Appl. No.: 10/116,095

(22) Filed: Apr. 4, 2002

(65) Prior Publication Data

US 2002/0177560 A1 Nov. 28, 2002

Related U.S. Application Data

(60) Provisional application No. 60/281,409, filed on Apr. 4, 2001.

(51) Int. Cl.[7] .......................... G01N 33/53; C12Q 1/37; C12N 9/50; A61K 38/48
(52) U.S. Cl. .......................... 435/975; 435/7.4; 435/23; 435/24; 435/219; 424/94.63
(58) Field of Search .......................... 435/975, 23, 24, 435/219; 424/94.63

(56) References Cited

U.S. PATENT DOCUMENTS

| | | | |
|---|---|---|---|
| 5,206,161 A | 4/1993 | Drayna et al. | 435/212 |
| 5,364,934 A | 11/1994 | Drayna et al. | 536/23.2 |
| 5,474,901 A | 12/1995 | Drayna et al. | 435/7.4 |
| 5,593,674 A | 1/1997 | Drayna et al. | 424/94.63 |
| 5,993,815 A | 11/1999 | Bajzar et al. | 424/145.1 |

OTHER PUBLICATIONS

Schatteman et al. "Assay of Procarboxypeptidase U, a Novel Determinant of the Fibrinolytic Cascade, in Human Plasma" Clinical Chemistry (1999) 45:6, pp. 807–813.*
Bajzar et al., 1995, "*Purification and characterization of TAFI, a thrombin–activable fibrinolysis inhibitor*", J. Biol. Chem. 270:14477–14484.
Boffa et al., 2000, "Roles of thermal instability and proteolytic cleavage in regulation of activated thrombin–activable fibrinolysis inhibitor", J. Biol. Chem. 275:12868–12878.
Boffa et al., 1998, "Plasma and recombinant thrombin–activable fibrinolysis inhibitor (TAFI) and activated TAFI compared with respect to glycosylation, thrombin/thrombomodulin–dependent activation, thermal stability, and enzymatic properties", J. Biol. Chem. 273:2127–2135.

Fava et al., 1994, "Vascular permeability factor/endothelial growth factor (VPF/VEGF): accumulation and expression in human synovial fluids and rheumatoid synovial tissue", J. Exp. Med. 180:341–346.
Hendriks et al., 1990, "Purification and characterization of a new arginine carboxypeptidase in human serum", Biochim. Biophys. Acta 1034:86–92.
Mosnier et al., 2001, "The defective down regulation of fibrinolysis in haemophilia A can be restored by increasing the TAFI plasma concentration", Thromb. Haemost. 86:1035–1039.
Mosnier et al., 2001, "The role of protein S in the activation of thrombin activatable fibrinolysis inhibitor (TAFI) and regulation of fibrinolysis", Thromb. Haemost. 86:1040–1046.
Mosnier et al., 2001, "Protein C inhibitor regulates the thrombin–thrombomodulin complex in the up– and down regulation of TAFI activation", Thromb. Haemost. 86:1057–1064.
Sumii and Lo, 2002, "Involvement of matrix metalloproteinase in thrombolysis–associated hemorrhagic transformation after embolic focal ischemia in rats", Stroke 33:831–836.
Taylor et al., 1985, "Whole blood clot lysis: in vitro modulation by activated protein C", Thromb. Res. 37:639–649.
Wang et al., 1994, "Carboxypeptidase U, a plasma carboxypeptidase with high affinity for plasminogen", J. Biol. Chem. 269:15937–15944.

* cited by examiner

*Primary Examiner*—Jean C. Witz
*Assistant Examiner*—S Hanley
(74) *Attorney, Agent, or Firm*—Jones Day (57) ABSTRACT

The invention is directed in part to a purified form of stabilized activated thrombin-activatable fibrinolysis inhibitor (TAFIa). The invention is further directed to a method of producing stabilized TAFIa. The invention is also directed to methods for therapeutic use of stabilized TAFIa such as in the treatment, prevention or management of diseases via an anti-coagulant effect. The invention is also directed to methods for therapeutic use of inhibitors of TAFIa such as in the treatment, prevention or management of diseases via a procoagulant effect. The invention is also directed to methods of diagnostic use of stabilized TAFIa such as a standard in a chromogenic or a fluorometric carboxypeptidase activity assay. The present invention is also directed to kits comprising stabilized TAFIa useful in measuring carboxypepetidase activity.

16 Claims, 8 Drawing Sheets

METHOD OF PREPARATION OF STABILIZED THROMBIN-ACTIVATABLE FIBRINOLYSIS INHIBITOR (TAFI) AND METHODS OF USE THEREOF

This application claims the benefit of U.S. Provisional Application No. 60/281,409, filed Apr. 4, 2001, which is incorporated by reference herein in its entirety.

1. FIELD OF THE INVENTION

The invention relates to a purified form of stabilized thrombin-activatable fibrinolysis inhibitor (TAFI), a method of producing stabilized TAFI, methods for therapeutic, prophylactic and diagnostic use of stabilized TAFI compositions and inhibitors thereof and kits comprising stabilized TAFI useful in measuring TAFI and other carboxypepetidase activity using the stabilized TAFI compositions of the invention as a standard.

2. BACKGROUND OF THE INVENTION

A proper balance between the activities of coagulation and fibrinolytic cascades is needed both to protect an organism from excessive blood loss upon injury and to maintain blood flow within the vascular system. The two opposing coagulation and fibrinolytic cascades are recognized to comprise a series of zymogen to enzyme conversions which terminate in the two respective proteolytic enzymes, thrombin and plasmin. These enzymes catalyze the formation and removal of fibrin within the circulatory system. Imbalances are characterized by either bleeding or thrombotic tendencies which may result in heart attacks or strokes in the organism.

Thrombin activatable fibrinolytic inhibitor (TAFI) is a 60 KDa glycoprotein present in human plasma that modulates fibrinolyisis in vivo. TAFI present in plasma is a proenzyme form which is most efficiently activated by proteolytic cleavage at Arg-92 with a thrombin-thrombomodulin complex. The proenzyme form of TAFI may also be activated by proteolytic cleavage by other proteolytic enzymes including, but not limited to, thrombin or plasmin. Upon activation of the TAFI proenzyme by proteolytic cleavage with thrombin-thrombomodulin, an active enzyme of 35 KDa is formed with carboxypeptidase-like activity (TAFIa). This molecule has also been referred to in the literature as plasma procarboxypeptidase B (PCPB), or plasma carboxypeptidase U (PCPU).

Modulation of fibrinolysis occurs when TAFIa cleaves C-terminal arginine and lysine residues of partially degraded fibrin, thereby inhibiting the stimulation of tissue plasminogen activator (t-PA) modulated plasminogen activation. The fibrinolytic system is activated primarily by t-PA which is provided by damaged cells in the blood vessel wall. t-PA converts circulating plasminogen to the active protease plasmin and can produce either slow enhancement of fibrinolysis or, when combined with fibrin, rapid enhancement of fibrinolysis. The effect of t-PA on fibrinolysis can be blocked by a class of inhibitors termed plasminogen activator inhibitors (PAIs), of which several have been identified.

Thrombomodulin is a component of the blood vessel wall which binds thrombin and changes its specificity from fibrinogen to protein C, resulting in a molecule possessing anticoagulant, rather than procoagulant, activity. The thrombin-thrombomodulin complex catalyzes cleavage of protein C to activated protein C, which results in down-regulation of the coagulation cascade by proteolytically inactivating the essential cofactors, Factor Va and VIIIa. In this manner, the body regulates coagulation cascade.

Studies such as that by Taylor et al., *Thromb. Res.* 37:639 (1985) have suggested that activated protein C is not only an anticoagulant, but also profibrinolytic, both in vivo and in vitro. Subsequently, it was determined that protein C only appears profibrinolytic because it prevents the thrombin-catalyzed activation of a previously unknown fibrinolysis inhibitor, whose precursor was isolated from plasma and designated as being TAFI.

TAFI was discovered independently in three different laboratories. In initially appeared as an unstable carboxypeptidase B-like molecule in human serum and was described by Hendriks et al., *Biochim. Biophys. Acta* 1034:86 (1990). A year later the cDNA for the molecule was cloned, its amino acid sequence was described, its activation by trypsin and its enzymatic properties toward synthetic carboxypeptidase B substrates was reported (see U.S. Pat. No. 5,206,161). In 1994, Wang et al., (*J. Biol. Chem.* 269:15937 (1994)) isolated the activated molecule and named it carboxypeptidase U ("U" being designated for unstable). Subsequently, Nesheim et al. (*J Biol. Chem.* 270:14477 (1995)) showed that the protein was both activated by thrombin and inhibits fibrinolysis, and designated the molecule TAFI. The co-identity of PCPB, PCPU, and TAFI has been established by their independent chromatographic behavior on plasminogen Sepharose® and the amino acid sequences present at the activation cleavage site.

Figure 1:
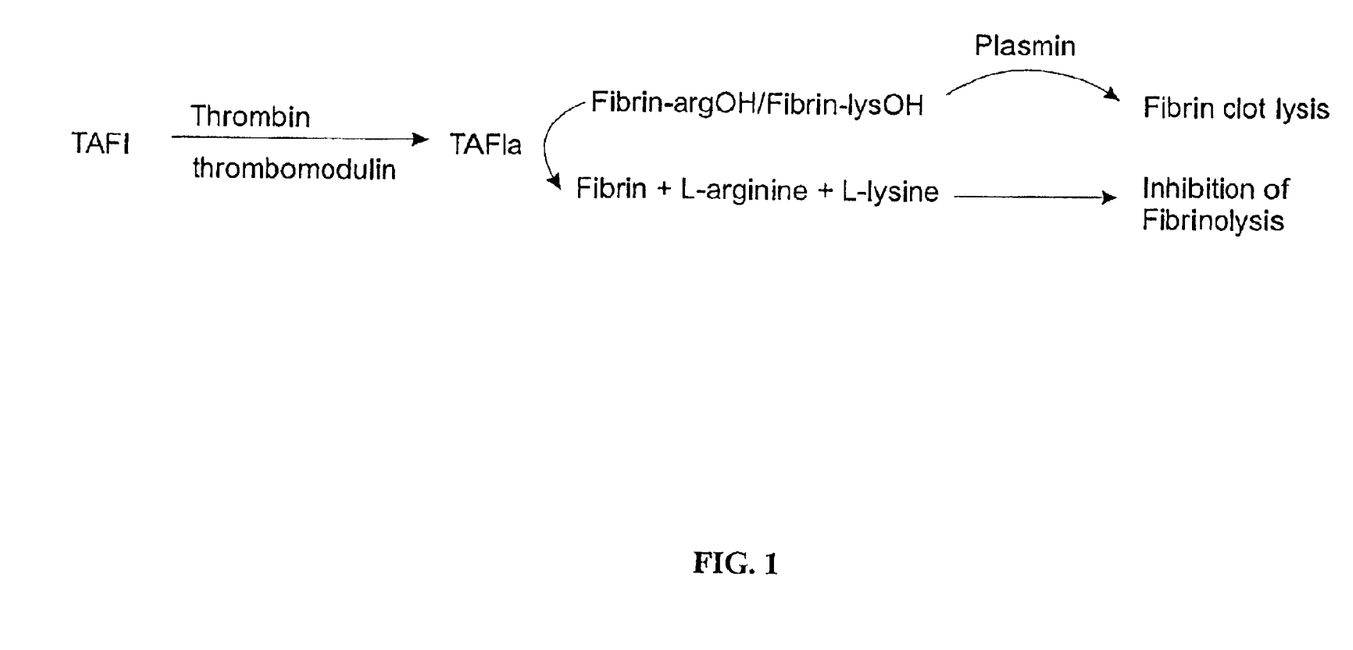
FIG. 1 is a schematic illustration of the mechanism of TAFI inhibition of fibrinolysis.
Figure 2:
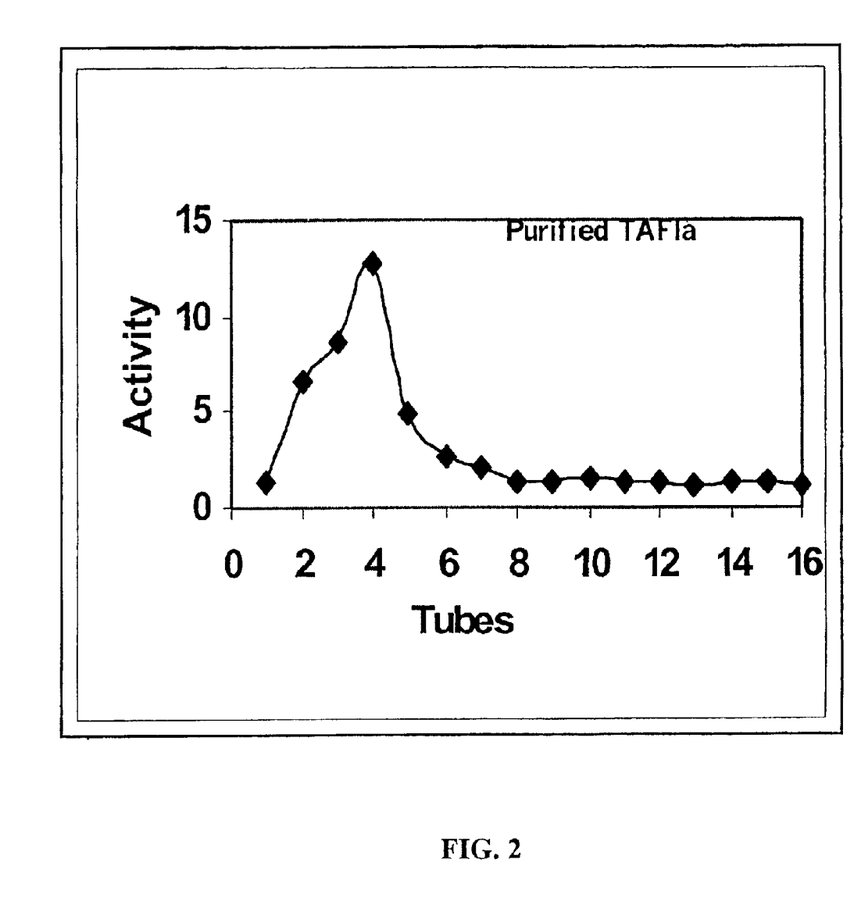
FIG. 2 shows the purification of stabilized TAFIa using affinity chromatography.
Figure 3:
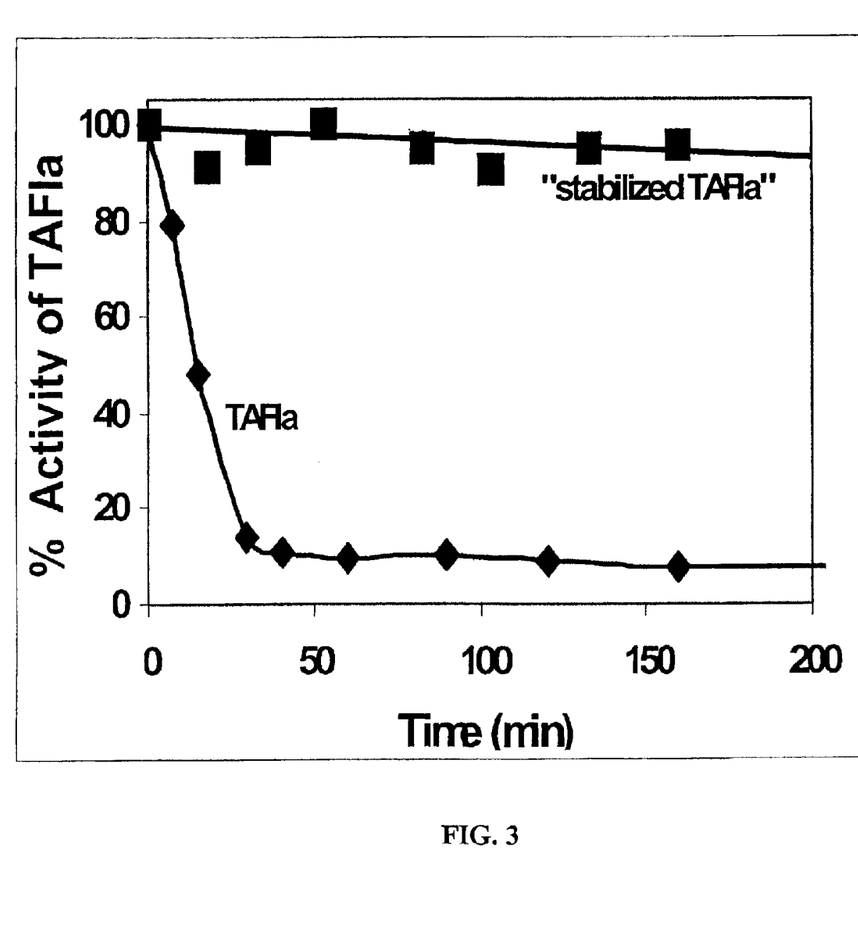
FIG. 3 illustrates the increased stability at room temperature of TAFIa prepared in a substantially calcium-free environment relative to TAFIa prepared using standard methods.

The mechanism of TAFI inhibition of fibrinolysis can be schematically described as depicted in FIG. 1.

Diagnostic assays for TAFIa may be useful in the prognosis or diagnosis of certain hemorrhagic or thrombotic diseases or disorders. Accordingly, there is a need in the art for effective carboxypeptidase activity assays.

As TAFIa is believed to play a central regulatory role in the fibrinolytic cascade, the manipulation of TAFIa levels or activity in biological fluids may have important therapeutic applications with respect to hemorrhagic disorders including, but not limited to, vascular and heart pathologies, and stroke. Inhibitors of TAFIa would enhance fibrinolysis and have an anti-coagulant effect (see U.S. Pat. No. 5,993, 815). Inhibitors of TAFIa could also be effective at treating or preventing the inflammation associated with arthritis as vascular endothelial growth factor (VEGF) is a potential substrate of TAFIa. VEGF has been linked with arthritis (Farva, R. A., *J. Exp. Med.* 180:341–6 (1994)).

Conversely, due to its ability to inhibit fibrinolysis, TAFIa itself may be useful as a therapeutic protein capable of acting as a procoagulant. In hemophilia A, a disease characterized by excessive bleeding, the addition of a protein mixture containing TAFIa to hemophilia A plasma has been reported to increase plasma clot lysis times (Mosnier, L. O. et al., *Thromb. Haemost.* 86:1035–9 (2001)). Additionally, thrombolytic therapy with tissue plasminogen activator (t-PA) for acute ischemic stroke remains complicated by risks of hemorrhagic transformation (Sumii T. and Lo E. H., *Stroke* 33:831–6 (2002)).

Unfortunately, the use of TAFIa as a therapeutic protein has not been feasible due to the inherent instability of the enzyme which has a half-life of less than 10 minutes at 37° C. Consequently, TAFIa is also extremely difficult to purify due to its highly unstable nature. Thus, there remains a need in the art for a method of producing a more thermally stable form of TAFIa, including purified forms of stabilized TAFIa, which could have widespread diagnostic use as well as therapeutic use in the treatment, prevention or management of hemorrhagic diseases or disorders.

Citation or identification of any reference in this section is not to be construed as such reference being prior art to the present application.

3. SUMMARY OF THE INVENTION

The present invention is based in part on the surprising discovery that TAFIa can be prepared in a stabilized form by activation of TAFI by proteolytic cleavage in a substantially calcium-free environment. In brief, the present invention is related to a method of preparing a stabilized form of TAFIa, methods for diagnostic and/or therapeutic use of stabilized TAFIa, methods of therapeutic use of TAFIa inhibitors, and kits comprising stabilized TAFIa useful in measuring carboxypepetidase activity, particularly TAFI activity.

In one embodiment, the present invention encompasses a method of producing a stabilized form of TAFIa, or a pharmaceutical composition thereof. In particular, the method of producing stabilized TAFIa comprises protease catalyzed activation of TAFI to TAFIa in a substantially calcium-free environment. In one embodiment, the proteolytic cleavage is catalyzed by thrombin. In another embodiment, the proteolytic cleavage is catalyzed by plasmin. In another embodiment, the proteolytic cleavage is catalyzed by a thrombin-thrombomodulin complex.

In one embodiment, the TAFIa is prepared from wild-type TAFI (e.g., purified from a native or recombinant source). The wild-type TAFI can be naturally occurring or recombinant. In another embodiment, the TAFIa is prepared from a mutant, variant, analog, polymorphism or derivative of TAFI, preferably where the mutant, variant, analog, polymorphism or derivative of TAFI can be processed to TAFIa that exhibits one or more activities of TAFIa. The mutant, variant, analog or derivative of TAFI can be naturally occurring or recombinantly produced.

In certain embodiments, stabilized TAFIa is then purified from remaining TAFI and other components of the activation reaction.

In another embodiment, the present invention is directed to a method of treating, preventing, managing or ameliorating the symptoms of a hemorrhagic disease or disorder comprising administering a therapeutically or prophylactically effective amount of stabilized TAFIa, or a pharmaceutical composition thereof, to a patient having such a disease or disorder. In certain embodiments the hemorrhagic disease or disorder includes, but is not limited to, hemophilia, von Willebrand disease (VWD), Henoch-Schonlein purpura, Factor deficiencies and hemostasis.

In another embodiment, the present invention is directed to a method of treating, preventing or managing bleeding side-effects associated with the administration of tissue plasminogen activator (t-PA), or an analog thereof, aspirin (particularly overdose) and other anti-coagulants, comprising administering a therapeutically or prophylactically effective amount of stabilized TAFIa, or a pharmaceutical composition thereof, to a patient having such a disease or disorder. In certain embodiments the bleeding side-effects include, but are not limited to, hemorrhagic transformation (HT).

In another embodiment, the present invention is directed to a method of treating, preventing or managing thrombotic diseases or disorders comprising administering a therapeutically or prophylactically effective amount of an inhibitor of TAFIa, or a pharmaceutically acceptable composition thereof, to a patient having such a disease or disorder. Inhibitors of TAFIa include, but are not limited to, captopril, captopril-phe, pro-phe-argininic acid, pro-trp-argininic acid, pro-tyr-argininic acid, pro-phe, pro-trp, pro-tyr and argininic acid. In certain embodiments the thrombotic diseases or disorders include, but are not limited to, heart attack, stroke, thromboembolic disease, acute myocardial infarction (AMI), deep vein thrombosis, acute ischemic stroke, massive pulmonary embolism, disseminated intravascular coagulation (DIC), anti-phospholipid syndrome, familial thrombophilia, sepsis, arthritis, fulminant hepatitis and thrombosis.

In another embodiment, the stabilized TAFIa, inhibitor of TAFIa, or pharmaceutical composition thereof, can be administered in combination with another prophylactic or therapeutic agent. In certain embodiments, the other therapeutic or prophylactic agent is useful for the treatment, prevention or management of a hemorrhagic or thrombotic disorder. In other embodiments, the therapeutic or prophylactic agent is not useful for the treatment, prevention or management of a hemorrhagic or thrombotic disorder. When used in combination with other prophylactic and/or therapeutic agents, the stabilized TAFIa, inhibitor of TAFIa, or pharmaceutical compositions thereof, can be administered prior to, subsequent to or concurrently with the other therapeutic or prophylactic agents.

In another embodiment, the present invention is directed to methods comprising the use of stabilized TAFIa as a standard in a diagnostic assay. In a preferred embodiment, the diagnostic assay allows for the determination of carboxypeptidase activity of a purified enzyme sample or biological samples such as, but not limited to, plasma, urine, serum, semen and cerebral or spinal fluid, by comparison to the activity of a stabilized TAFIa standard. In a more preferred embodiment, the diagnostic assay measures TAFIa activity of a purified enzyme sample or biological samples such as plasma. In a preferred embodiment, the carboxypeptidase activity of TAFIa is measured in a chromogenic assay.

In another embodiment, the invention is directed to a kit comprising the components of the chromogenic carboxypeptidase diagnostic assay. In a certain embodiment, the kit comprises a stabilized TAFIa standard; a specially formulated developer comprising a carboxypeptidase substrate such as hippuryl-L-lysine or the tetrapeptide pro-phe-gly-lys (PFGK); lysine oxidase; horseradish peroxidase (HRP); a chromogenic substrate of HRP, such as O-phenylene diamine (OPD) or TMB; in any appropriate buffer, e.g., 200 mM Tris-HCl, pH 7.4 buffer.

In another embodiment, the present invention is directed to a method of measuring carboxypeptidase activity in a fluorescent-based assay using stabilized TAFIa as a standard. In a preferred embodiment, the carboxypeptidase activity of TAFIa is measured in the fluorescent-based assay.

In another embodiment, the invention is directed to a kit comprising the components of the fluorescent-based diagnostic assay. In a certain embodiment, the kit comprises a stabilized TAFIa standard; a specially formulated developer comprising a carboxypeptidase substrate such as hippuryl-L-lysine or the tetrapeptide pro-phe-gly-lys (PFGK); lysine oxidase; horseradish peroxidase (HRP); a chromogenic substrate of HRP, such as O-phenylene diamine (OPD) or TMB; in any appropriate buffer, e.g., 200 mM Tris-HCl, pH 7.4 buffer.

In another embodiment, the present invention is directed a method of using the tetrapeptide pro-phe-gly-lys (PFGK), hippuryllysine or hippurylarginine as a substrate for TAFIa in a diagnostic carboxypeptidase activity assay.

These and other aspects of this invention will be evident upon reference to the following detailed description and figures. To that end, certain patent and other documents are cited herein to more specifically set forth various aspects of this invention. Each of these documents are hereby incorporated by reference herein in its entirety.

3.1 Definitions

The term "active" as used to describe stabilized TAFIa means TAFIa with a $V_{max}$ preferably above about 10 μmol/min, more preferably, above about 15 μmol/min, more preferably above about 20 μmol/min, and most preferably, above about 25 μmol/min.

The terms "analog", "polymorphism" and "variant" as used herein refers to a polypeptide that possesses a similar or identical function as a particular protein (e.g., TAFIa), or a fragment thereof, but does not necessarily comprise a similar or identical amino acid sequence or structure of that protein complex or a fragment thereof. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of the protein or protein complex or a fragment thereof as described herein (e.g., human or murine TAFI or TAFIa, e.g., having an amino acid sequence of accession No. NP_001863 or NP_062749, respectively, or the mature protein thereof); (b) a polypeptide encoded by a nucleotide sequence that hybridizes under stringent conditions to a nucleotide sequence encoding a protein or protein complex of the invention, or fragment thereof, as described herein of at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding the protein or protein complex of the invention or a fragment thereof as described herein. A polypeptide with similar structure to a protein or protein complex of the invention or a fragment thereof as described herein refers to a polypeptide that has a similar secondary, tertiary or quaternary structure of said protein or protein complex or a fragment thereof as described herein. The structure of a polypeptide can be determined by methods known to those skilled in the art, including but not limited to, X-ray crystallography, nuclear magnetic resonance, and crystallographic electron microscopy.

The term "derivative" as used herein refers to a polypeptide that comprises an amino acid sequence of a protein (e.g., TAFIa) or protein complex of the invention or a fragment thereof as described herein that has been altered by the introduction of amino acid residue substitutions, deletions or additions. The term "derivative" as used herein also refers to a protein or protein complex of the invention or a fragment thereof that has been modified, i.e., by the covalent attachment of any type of molecule to the polypeptide. For example, but not by way of limitation, a protein or protein complex or a fragment thereof may be modified, e.g., by glycosylation, acetylation, pegylation, phosphorylation, amidation, derivatization by known protecting/blocking groups, proteolytic cleavage, linkage to a cellular ligand or other protein, etc. A derivative of a protein or protein complex or a fragment thereof may be modified by chemical modifications using techniques known to those of skill in the art, including, but not limited to specific chemical cleavage, acetylation, formylation, metabolic synthesis of tunicamycin, etc. Further, a derivative of a protein or protein complex or a fragment thereof may contain one or more non-classical amino acids. A polypeptide derivative possesses a similar or identical function as a protein or protein complex or a fragment thereof described herein.

The phrase "free calcium" means calcium that is not bound, chelated or otherwise sequestered.

The phrase "modulation of fibrinolysis" means the inhibition or activation of the fibrinolytic cascade which may have an anti-coagulant or procoagulant effect.

The phrases "substantially calcium-free environment" or "substantially free from calcium" mean a free calcium concentration (i.e., not chelated or otherwise sequestered) of less than 100 μM, more preferably less than 10 μM, more preferably less than 1 μM, more preferably less than 500 nM, more preferably less than 100 nM, more preferably less than 1 nM, more preferably less than 100 pM, and most preferably less than 1 pM.

"TAFIa inhibitor" or "inhibitors of TAFIa" means any molecule that blocks, reduces or retards the cleavage of fibrin or other substrates by TAFIa.

The phrase "stabilized TAFIa" means TAFIa that has a half-life of at least one hour at room temperature, more preferably of at least two hours, more preferably of at least four hours, more preferably of at least eight hours, more preferably of at least twelve hours, more preferably of at least twenty-four hours and most preferably of at least forty-eight hours.

The phrase "purified TAFIa" means a TAFIa composition that has TAFIa as predominantly a single-band by coomassie-stained, or more preferably, silver-stained, SDS-PAGE gel. Preferably, the TAFIa is a single band on a coomassie-stained, or more preferably, silver-stained, SDS-PAGE gel. Preferably, the purified TAFIa is substantially free from thrombin-thrombomodulin. Preferably, TAFIa has been purified after activation by a purification step such as including, but not limited to, size-exclusion chromatography, affinity chromatography or ammonium sulfate precipitation. In a preferred embodiment, TAFIa is purified by affinity chromatography on a potato tuber carboxypeptidase inhibitor (PTCI)-Sepharose column. In specific embodiments, the purified TAFIa ia at least 75%, 80%, 85%, 90%, 95%, 99% or preferably at least 99.5% of the composition.

The term "prophylactic agent" means an agent capable of preventing or reducing the risks or incidence of a disease or disorder in a patient. In one embodiment, the prophylactic agent is one which is capable of preventing a hemorrhagic or thrombotic disorder.

The phrase "prophylactically effective amount" refers to that amount of the prophylactic agent sufficient to result in the prevention or reduction in the risk or incidence of the hemorrhagic or thrombotic disorder. Further, a prophylactically effective amount with respect to a prophylactic agent of the invention means that amount of prophylactic agent alone, or in combination with other agents, that provides a prophylactic benefit in the prevention of the hemorrhagic or thrombotic disorder.

The term "therapeutic agent" means an agent capable of modifying, controlling, delaying or reversing a disease or disorder or ameliorating the symptoms of a disease or disorder in a patient. In one embodiment, the therapeutic agent is one which is capable of modifying, controlling, delaying, reversing or ameliorating the symptoms of a hemorrhagic or thrombotic disorder.

The phrase "therapeutically effective amount" refers to that amount of the therapeutic agent sufficient to modify, control, reverse or ameliorate the symptoms of the hemorrhagic or thrombotic disorder. A therapeutically effective amount may refer to the amount of therapeutic agent sufficient to delay, minimize, reverse or ameliorate the symptoms of the hemorrhagic or thrombotic disorder. A therapeutically effective amount may also refer to the amount of the therapeutic agent that provides a therapeutic benefit in the treatment or management of the hemorrhagic or thrombotic disorder. Further, a therapeutically effective amount with respect to a therapeutic agent of the invention means that amount of therapeutic agent alone, or in combination with other therapies, that provides a therapeutic benefit in the treatment or management of the hemorrhagic or thrombotic disorder, including the amelioration of symptoms associated with the hemorrhagic or thrombotic disorder being treated.

The phrase "in combination" refers to the use of more than one prophylactic and/or therapeutic agents against a hemorrhagic or thrombotic disease or disorder.

The term "patient" refers to a mammal such as a non-primate (e.g., cows, pigs, horses, cats, dogs, mice, rats etc.) or a primate (e.g., monkeys and humans). Preferably the patient is a human.

The terms "manage", "managing" and "management" refer to the beneficial effects that a patient derives from a prophylactic or therapeutic agent, which does not result in a cure of the disorder. In certain embodiments, a patient is administered one or more prophylactic or therapeutic agents to "manage" a disease or disorder, or symptoms associated with the disease or disorder, so as to prevent the progression or worsening of the disease or disorder.

The terms "prevent", "preventing" and "prevention" refer to the prevention of the recurrence, spread or onset of the hemorrhagic or thrombotic disease or disorder, or symptoms associated with the disease or disorder, in a patient resulting from the administration of a prophylactic or therapeutic agent.

The terms "treat", "treating" and "treatment" refer to the, modification, control, reversal or amelioration of the symptoms of the hemorrhagic or thrombotic disease or disorder that results from the administration of one or more prophylactic or therapeutic agents. In certain embodiments, such terms refer to the minimizing or delay of the hemorrhagic or thrombotic disease or disorder resulting from the administration of one or more prophylactic or therapeutic agents to a patient with such a disease or disorder.

The term "t-PA" refers to native t-PA and recombinant t-PA as well as homologs, derivatives and polymorphisms of t-PA that retain the catalytic activity of native t-PA.

4. BRIEF DESCRIPTION OF THE FIGURES

FIG. 1.

FIG. 2.

FIG. 3.

FIG. 4.

FIG. 5.

FIG. 6.

FIG. 7.

FIG. 8.

5. DETAILED DESCRIPTION OF THE INVENTION 5.1 Preparation of Stabilized TAFIa

The present invention provides a method of producing a stabilized form of TAFIa useful in diagnostic and therapeutic methods. In particular, the method of producing stabilized TAFIa comprises activation of TAFI to TAFIa by proteolytic cleavage in a substantially calcium-free environment.

In one embodiment, the TAFIa is prepared from wild-type TAFI (e.g., purified from a native or recombinant source). The wild-type TAFI can be naturally occurring or recombinant. In another embodiment, the TAFIa is prepared from a mutant, variant, analog, polymorphism or derivative of TAFI, preferable where the mutant, variant, analog, polymorphism or derivative or TAFI can be processed to TAFIa that exhibits one or more activities of TAFIa. The mutant, variant, analog, polymorphism or derivative of TAFI can be naturally occurring or recombinant. In a particular embodiment, the TAFIa derived from activation of the mutant TAFI has a longer half-life than the TAFIa derived from wild-type TAFI. In a preferred embodiment, the mutant TAFIa is an Ile-325 mutant with a half-life of 15 minutes at 37° C. (Nesheim et al., *J. Biol. Chem.* 277:1021 (2002)). Preferably, the TAFI is human TAFI (accession No. NP_001863; Boffa, M. B., et al., *Biochemistry* 38:6547–58 (1999)), but may be any other TAFI analog, e.g., mouse (accession No. NP_062749), rat, bovine, porcine, etc. Preferably, for therapeutic uses the TAFI is from the same species as the subject being treated.

In particular, the method of producing stabilized TAFIa comprises protease catalyzed activation of TAFI to TAFIa in a substantially calcium-free environment. In one embodiment, the proteolytic cleavage is catalyzed by thrombin. In another embodiment, the proteolytic cleavage is catalyzed by plasmin. In another embodiment, the proteolytic cleavage is catalyzed by a thrombin-thrombomodulin complex. TAFIa is typically produced by proteolytic cleavage with thrombin-thrombomodulin in a buffer which contains calcium. The calcium is necessary for optimal activity of the thrombin-thrombomodulin complex. The TAFIa prepared in this manner is highly unstable with a half-life of less than 10 minutes at 37° C. and 30–40 minutes at room temperature. However, as discovered by the present inventors, TAFIa that is produced by thrombin-thrombomodulin cleavage in a substantially calcium-free environment is highly stable (i.e., has a much longer half-life) at temperatures up to 37° C. The stabilized TAFIa of the present invention preferably has a half-life of more than 8 hours at room temperature and more than 5 hours at 37° C. The activity of the stabilized form of TAFIa is decreased by the addition of calcium.

In one embodiment, the present invention encompasses a method of producing a stabilized form of TAFIa, or a pharmaceutical composition thereof. In particular, the method of producing stabilized TAFIa comprises thrombin-thrombomodulin catalyzed activation of TAFI to TAFIa in a substantially calcium-free environment. In a preferred embodiment, there is less than 1 μM free calcium present in the thrombin-thrombomodulin catalyzed activation of TAFI to TAFIa. In a more preferred embodiment, there is less than 500 nM free calcium present in the thrombin-thrombomodulin catalyzed activation of TAFI to TAFIa. In a more preferred embodiment, there is less than 100 nM free calcium present in the thrombin-thrombomodulin catalyzed activation of TAFI to TAFIa. In a more preferred embodiment, there is less than 1 nM free calcium present in the thrombin-thrombomodulin catalyzed activation of TAFI to TAFIa. In a more preferred embodiment, there is less than 100 pM free calcium present in the thrombin-thrombomodulin catalyzed activation of TAFI to TAFIa. In a most preferred embodiment, there is less than 1 pM free calcium present in the thrombin-thrombomodulin catalyzed activation of TAFI to TAFIa.

In another embodiment, the substantially calcium-free environment can be achieved by chelation of free calcium with a chelator such as citrate. In another embodiment, there is an undetectable level of chelated calcium.

In a preferred embodiment, the stabilized TAFIa has a half-life of at least 30 minutes at 37° C. In a more preferred embodiment, the stabilized TAFIa has a half-life of at least one hour at 37° C. In a more preferred embodiment, the stabilized TAFIa has a half-life of at least two hour s at 37° C. In a more preferred embodiment, the stabilized TAFIa has a half-life of at least four hours at 37° C. In a more preferred embodiment, the stabilized TAFIa has a half-life of at least five hours at 37° C. In a more preferred embodiment, the stabilized TAFIa has a half-life of at least eight hours at 37° C. In a more preferred embodiment, the stabilized TAFIa has a half-life of at least twelve hours at 37° C. In a most preferred embodiment, the stabilized TAFIa has a half-life of at least twenty-four hours at 37° C.

In a preferred embodiment, the stabilized TAFIa has a half-life of at least one hour at room temperature. In a more preferred embodiment, the stabilized TAFIa has a half-life of at least two hours at room temperature. In a more preferred embodiment, the stabilized TAFIa has a half-life of at least four hours at room temperature. In a more preferred embodiment, the stabilized TAFIa has a half-life of at least eight hours at room temperature. In a more preferred embodiment, the stabilized TAFIa has a half-life of at least twelve hours at room temperature. In a more preferred embodiment, the stabilized TAFIa has a half-life of at least twenty-four hours at room temperature. In a most preferred embodiment, the stabilized TAFIa has a half-life of at least forty-eight hours at room temperature.

Preferably, the stabilized TAFIa has a half-life of at least one hour at room temperature and thirty minutes at 37° C. More preferably, the stabilized TAFIa has a half-life of at least two hours at room temperature and one hour at 37° C. More preferably, the stabilized TAFIa has a half-life of at least four hours at room temperature and two hours at 37° C. More preferably, the stabilized TAFIa has a half-life of at least eight hours at room temperature and four hours at 37° C. More preferably, the stabilized TAFIa has a half-life of at least twelve hours at room temperature and eight hour at 37° C. More preferably, the stabilized TAFIa has a half-life of at least twenty-four hours at room temperature and twelve hours at 37° C. More preferably, the stabilized TAFIa has a half-life of at least forty-eight hours at room temperature and twenty-four hours at 37° C.

Figure 5:
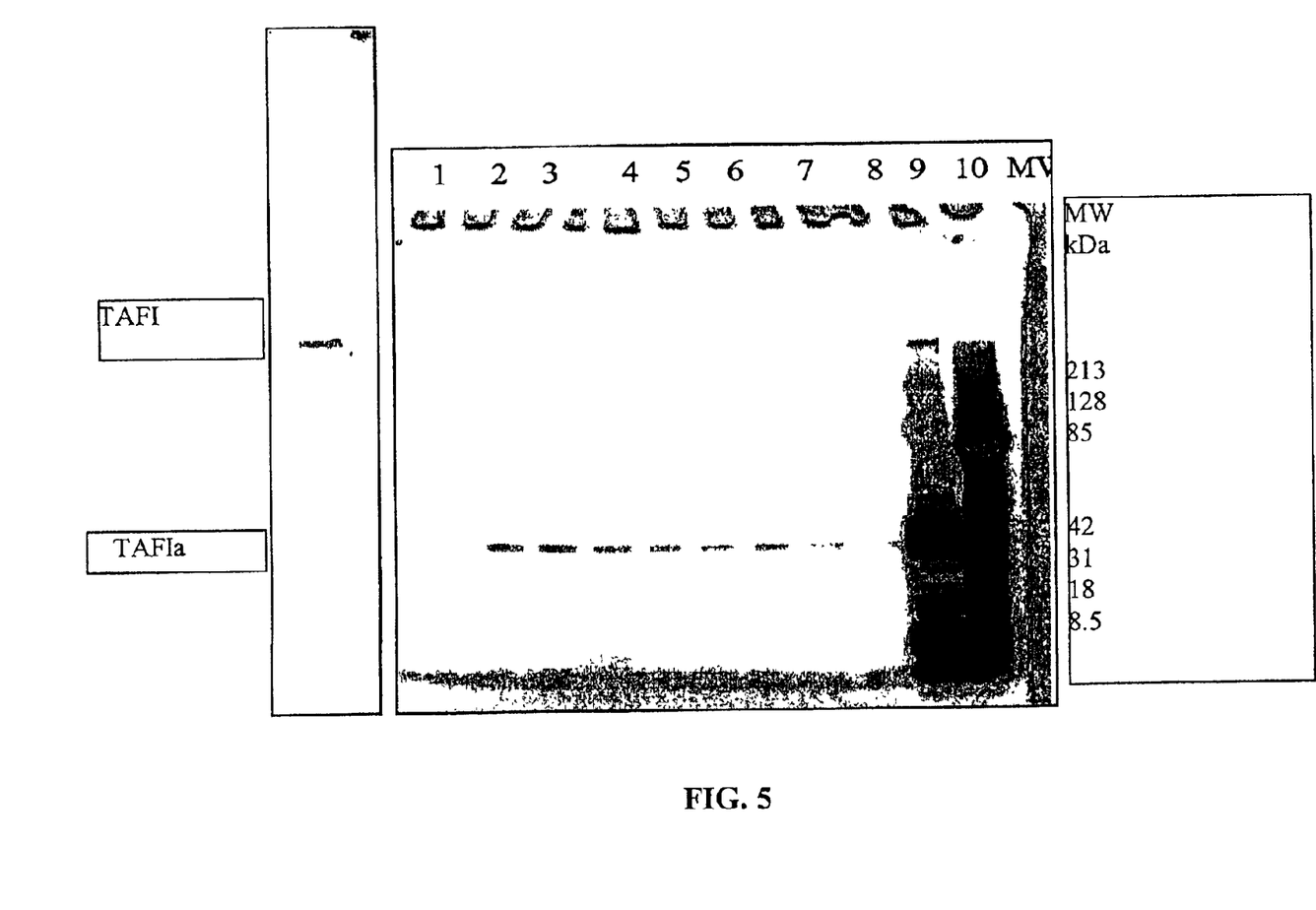
FIG. 5 shows purified TAFIa as a single band on a silver stained SDS-PAGE gel.
Figure 6:
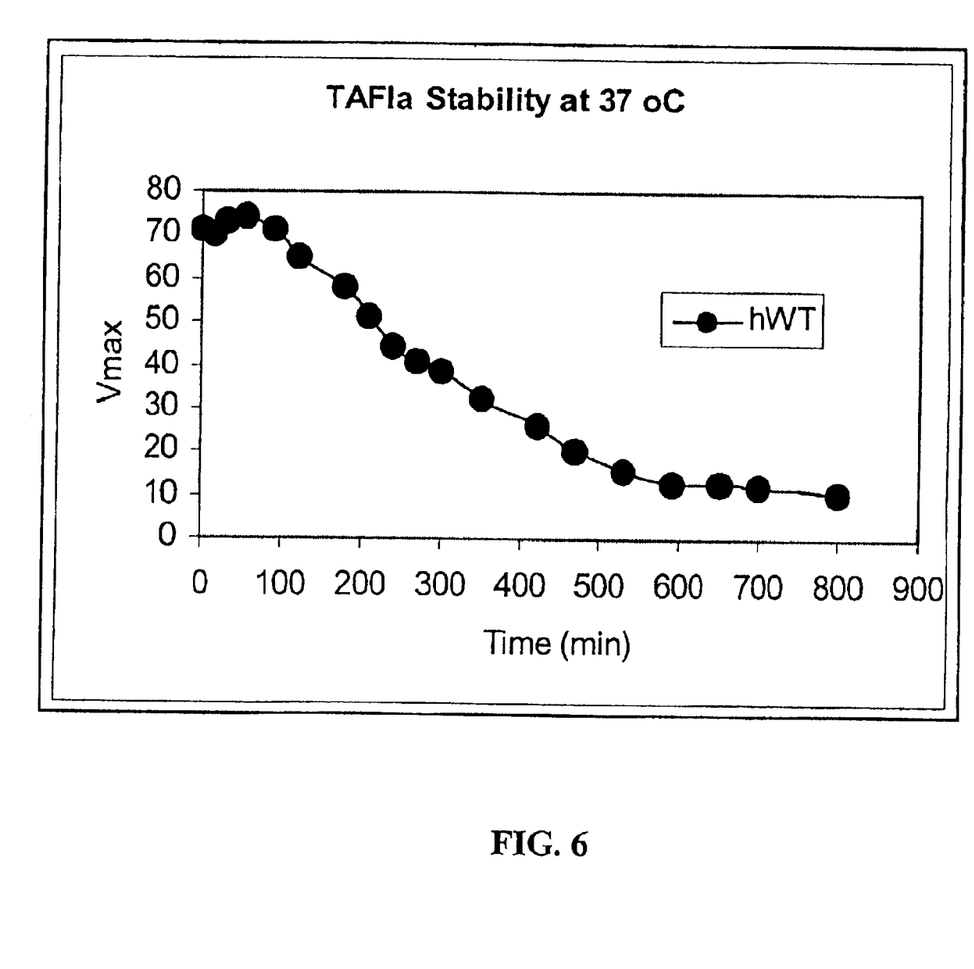
FIG. 6 illustrates the increased stability at 37° C. of TAFIa prepared in a substantially calcium-free environment relative to TAFIa prepared using standard methods.
Figure 7:
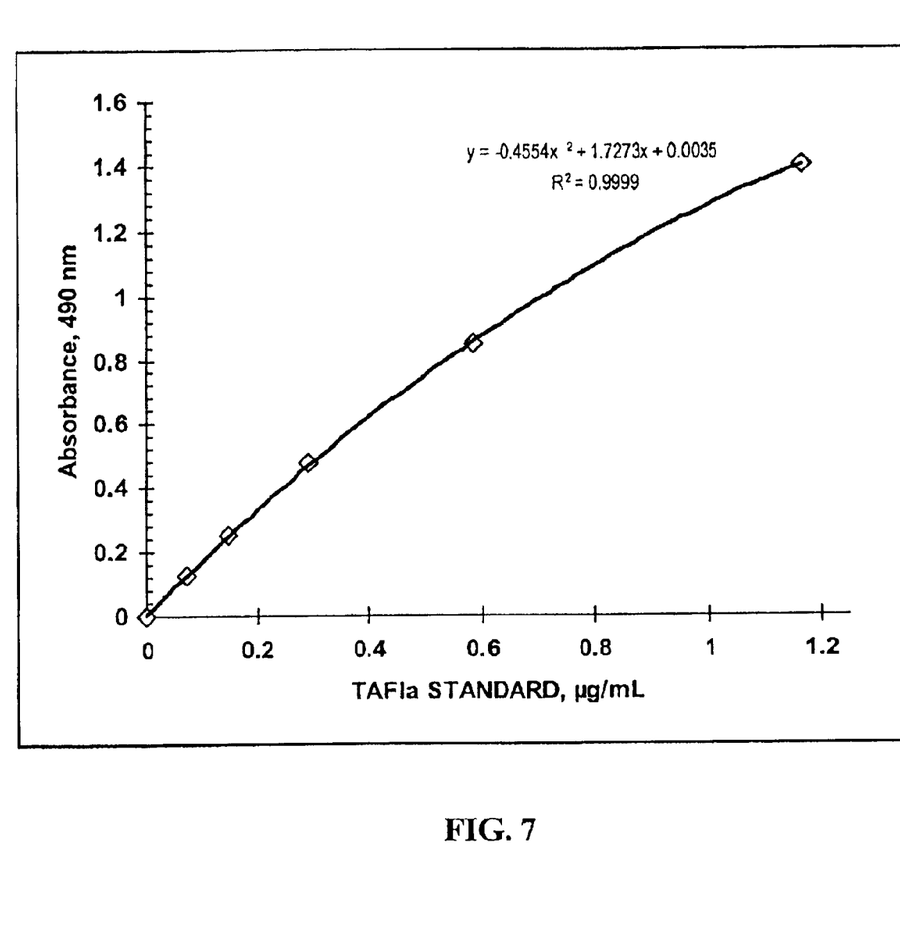
FIG. 7 shows a standard curve prepared using stabilized TAFIa in the chromogenic assay described herein.
Figure 8:
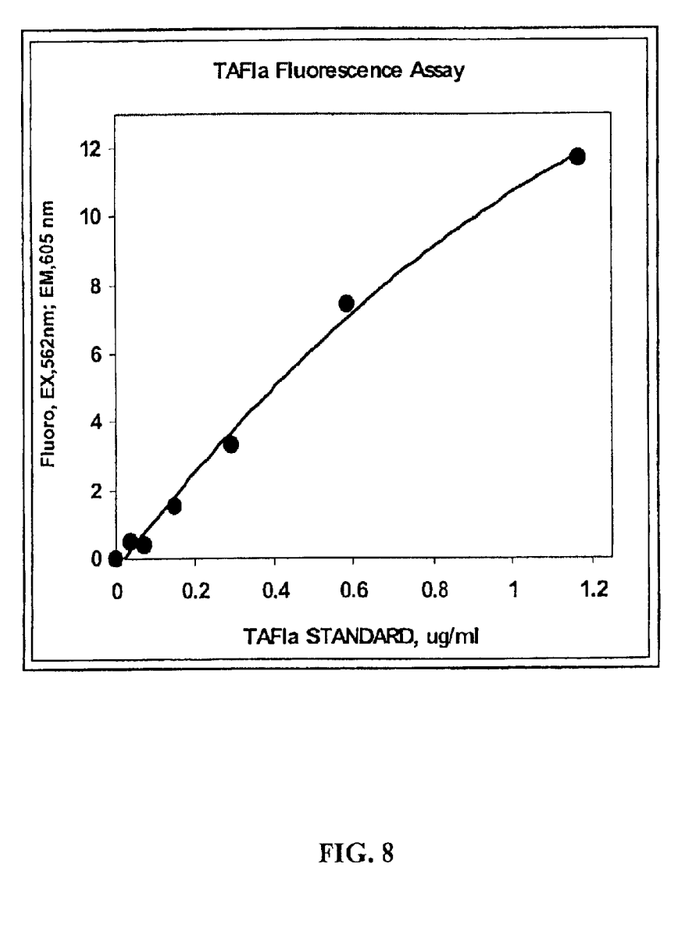
FIG. 8 shows a standard curve prepared using stabilized TAFIa in the fluorometric assay described herein.

In certain embodiments, the invention encompasses a purified, stable form of TAFIa. In a preferred embodiment, the purified, stabilized form of TAFIa is substantially free of calcium. Stabilized TAFIa can be purified from remaining TAFI, the thrombin-thrombomodulin complex, the proteolytic fragment of TAFI and other components of the activation reaction by purification methods including, but not limited to, affinity chromatography, size exclusion chromatography or ammonium sulfate precipitation. In a preferred embodiment, the TAFIa reaction mixture is applied to a potato tuber carboxypeptidase inhibitor (PTCI)-sepharose column which specifically binds TAFIa but not TAFI. The N-terminal fragment of TAFI which is cleaved by thrombin-thrombomodulin during activation does not bind to the PTCI-sepharose column. Purified TAFIa preferably appears predominantly as a silver-stained single band on an SDS-PAGE gel (see FIG. 5).

5.2 Prophylactic/Therapeutic Methods

The present invention encompasses methods for treating, preventing, or managing a hemorrhagic and/or thrombotic disease or disorder or any disease or disorder associated with an aberrant level of TAFIa or which can be treated, prevented or managed by modulation (e.g., increasing or decreasing) of TAFIa activity.

The hemorrhagic and thrombotic diseases occur, in part, because the normal balance between the coagulation and fibrinolytic cascades has been affected, altered or shifted. The methods of the present invention allow the balance of the cascades to be shifted by individually increasing or decreasing one of the respective cascades without affecting the other.

In particular, the present invention is directed to a method of treating, preventing or managing a hemorrhagic disease or disorder comprising administering a therapeutically or prophylactically effective amount of stabilized TAFIa, or a pharmaceutical composition thereof, to a patient. In certain embodiments the hemorrhagic disorder includes, but is not limited to, hemophilia, von Willebrand disease (VWD), Henoch-Schonlein purpura, Factor deficiencies and hemostasis.

In another embodiment, the present invention is directed to a method of treating, preventing or managing bleeding side-effects associated with the administration of tissue plasminogen activator (t-PA), urokinase plasminogen activator(u-PA), streptokinase, staphylokinase, plasminogen or analogs thereof, heparin, low molecular weight heparin, aspirin (e.g., overdose) or any other anti-coagulant (e.g., overdose) comprising administering a therapeutically or prophylactically effective amount of stabilized TAFIa, or a pharmaceutical composition thereof, to a patient. In certain embodiments the bleeding side-effects include, but are not limited to, hemorrhagic transformation (HT).

In another embodiment, the present invention is directed to a method of treating, preventing or managing a thrombotic disease or disorder comprising administering a therapeutically or prophylactically effective amount of an inhibitor of TAFIa, or a pharmaceutical composition thereof, to a patient. In certain embodiments the thrombotic diseases or disorders include, but are not limited to, heart attack, stroke, thromboembolic disease, acute myocardial infarction (AMI), deep vein thrombosis, acute ischemic stroke, massive pulmonary embolism, disseminated intravascular coagulation (DIC), familial thrombophilia, sepsis, arthritis, fulminant hepatitis and thrombosis.

In another embodiment, the stabilized TAFIa, inhibitor of TAFIa, or pharmaceutical composition thereof, can be administered in combination with another prophylactic or therapeutic agent. When used in combination with other prophylactic and/or therapeutic agents, the stabilized TAFIa, inhibitor of TAFIa, or pharmaceutical composition thereof can be administered prior to, subsequent to or concurrently with one or more other therapeutic or prophylactic agents. In one embodiment, the stabilized TAFIa, inhibitor of TAFIa, or pharmaceutical composition thereof is administered concurrently with one or more therapeutic or prophylactic agents in the same pharmaceutical composition. In another embodiment, the stabilized TAFIa, inhibitor of TAFIa, or pharmaceutical composition thereof is administered concurrently with one or more other therapeutic or prophylactic agents in separate pharmaceutical compositions. In certain embodiments, the other therapeutic or prophylactic agent is useful for the treatment, prevention or management of a hemorrhagic and/or thrombotic disorder. In other embodiments, the therapeutic or prophylactic agent is not useful for the treatment, prevention or management of a hemorrhagic and/or thrombotic disorder. In certain embodiments, the therapeutic or prophylactic agent includes, but is not limited to, t-PA, heparin, aspirin, Factor VII, Factor VIII, Factor IX, amino caproic acid, activated protein C, thrombin, fibrinogen, cryofractionalized plasma, actothrombin, low molecular weight heparin, hirudin, plasminogen, streptokinase, staphylokinase, urokinase or hirulong.

Suitable regimens can be selected by one skilled in the art by considering such factors and by following, for example, dosages reported in the literature and recommended in the *Physician's Desk Reference* (56$^{th}$ ed., 2002).

5.2.1. Patient Population

The invention provides methods for treating, preventing, or managing hemorrhagic and/or thrombotic disorders, or any other disease or disorder associated with aberrant levels of TAFIa or which can be treated, prevented or managed by modulation (e.g., increasing or decreasing) of TAFIa activity, by administrating to a patient a therapeutically or prophylactically effective amount of stabilized TAFIa, an inhibitor of TAFIa, or pharmaceutical composition thereof. The patient is preferably a mammal such as a non-primate (e.g., cows, pigs, horses, cats, dogs, mice, rats etc.) or a primate (e.g., monkeys, such as cynomolgous monkeys, and humans). In a preferred embodiment, the patient is a human.

The invention also encompasses methods for treating patients that are receiving or have received any other treatment useful for the prevention or hemorrhagic and/or thrombotic diseases or disorders. Using the methods of the present invention, patients can be treated for the prevention, treatment or management of hemorrhagic and/or thrombotic diseases or disorders, including, but not limited to, hemophilia, heart attack, stroke, thromboembolic disease, von Willebrand disease (VWD), acute myocardial infarction (AMI), deep vein, thrombosis, acute ischemic stroke, massive pulmonary embolism, disseminated intravascular coagulation (DIC), familial thrombophilia, sepsis, arthritis, Fulminant hepatitis, Henoch-Schonlein purpura, hemostasis and thrombosis, or any disease or disorder characterized by excessive bleeding or clotting. In another embodiment, the methods of the present invention are useful for the amelioration of symptoms associated with hemorrhagic and/or thrombotic diseases or disorders. The methods and compositions of the invention can be used with one or more conventional or experimental therapies that are used to prevent, treat or manage hemorrhagic and/or thrombotic diseases or disorders.

In one embodiment, the invention provides methods for treating, preventing, or managing hemorrhagic and/or thrombotic diseases or disorders by administrating a therapeutically or prophylactically effective amount of stabilized TAFIa, an inhibitor of TAFIa, or a pharmaceutical composition thereof to a patient currently undergoing alternative treatment for a hemorrhagic or thrombotic disease or disorder.

In another embodiment, the invention provides methods for treating, preventing, or managing hemorrhagic and/or thrombotic diseases or disorders by administrating a therapeutically or prophylactically effective amount of stabilized TAFIa, an inhibitor of TAFIa, or a pharmaceutical composition thereof to a patient who has previously undergone treatment for a hemorrhagic or thrombotic disease or disorder.

In another embodiment, the invention provides methods for treating, preventing, or managing hemorrhagic and/or thrombotic diseases or disorders by administrating a therapeutically or prophylactically effective amount of stabilized TAFIa, an inhibitor of TAFIa, or a pharmaceutical composition thereof to a patient who has never undergone treatment for a hemorrhagic or thrombotic disease or disorder.

5.2.2. Combination Therapies

According to the invention, therapy by administration of stabilized TAFIa, an inhibitor of TAFIa, or a pharmaceutical composition thereof is combined with the administration of one or more therapeutic or prophylactic agents such as, but not limited to, anti-coagulant or procoagulant agents. When used in combination with other prophylactic and/or therapeutic agents, the stabilized TAFIa, inhibitor of TAFIa, or pharmaceutical composition thereof can be administered prior to, subsequent to or concurrently with the other therapeutic or prophylactic agents. Examples of anti-coagulant agents include, but are not limited to, t-PA (or analogs thereof), heparin, low molecular weight heparin, aspirin, actothrombin, hirudin, plasminogen, streptokinase, staphylokinase, urokinase or hirulong. Examples of procoagulant agents include, but are not limited to, amino caproic acid, Factor VII, Factor VIII, Factor IX, Factor VIIa, Factor IXa, activated protein C, thrombin, fibrinogen and cryofractionalized plasma.

In one embodiment, stabilized TAFIa, an inhibitor of TAFIa, or a pharmaceutical composition thereof is administered in combination with surgery. The administration can be either prior to surgery, after surgery or concomitant with surgery. Examples of such surgeries include, but are not limited to, organ transplant surgery, cardiopulmonary bypass surgery, coronary angioplasty, open heart surgery, heart valve surgery or removal of atherosclerotic plaques 5.2.3 Pharmaceutical Compositions Pharmaceutical compositions of the present invention comprise a prophylactically or therapeutically effective amount of stabilized TAFIa (preferably purified) or an inhibitor of TAFIa, alone or in combination with another prophylactic or therapeutic agent, and a pharmaceutically acceptable carrier. Preferably, compositions of the invention comprise a prophylactically or therapeutically effective amount of TAFIa or an inhibitor of TAFIa, and a pharmaceutically acceptable carrier.

The term "carrier" refers to a diluent, adjuvant, excipient, or vehicle with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propyleneglycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in "Remington's Pharmaceutical Sciences" by E. W. Martin.

In a preferred embodiment, the compounds of the invention are formulated in accordance with routine procedures as a pharmaceutical composition adapted for intravenous administration to human beings. Typically, compounds of the invention for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

Compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharin, cellulose, magnesium carbonate, etc. Such vehicles are preferably of pharmaceutical grade.

Further, the effect of the compounds of this invention may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film which resists dissolution for a predictable period of time. Even the parenteral preparations may be made long-acting, by dissolving or suspending the compound in oily or emulsified vehicles which allow it to disperse only slowly in the serum.

5.2.4 Routes of Administration

Methods of administering stabilized TAFIa, an inhibitor of TAFIa, or a pharmaceutical composition thereof include, but are not limited to, parenteral administration (e.g., intradermal, intramuscular, intraperitoneal, intravenous and subcutaneous), epidural, and mucosal (e.g., intranasal, rectal, vaginal, sublingual, buccal or oral routes). In a specific embodiment, stabilized TAFIa, an inhibitor of TAFIa, or a pharmaceutical composition thereof is administered intramuscularly, intravenously, or subcutaneously. The stabilized TAFIa, an inhibitor of TAFIa, or pharmaceutical composition thereof may also be administered by infusion or bolus injection and may be administered together with other therapeutic or prophylactic agents. Administration can be local or systemic. The stabilized TAFIa, an inhibitor of TAFIa, or pharmaceutical composition thereof may also be administered by inhalation or insufflation (either through the mouth or the nose). In a preferred embodiment, local or systemic parenteral administration is used.

In specific embodiments, it may be desirable to administer the stabilized TAFIa, an inhibitor of TAFIa, or a pharmaceutical composition thereof, locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the stabilized TAFIa, an inhibitor of TAFIa, or a pharmaceutical composition thereof can be formulated as a suppository, with traditional binders and vehicles such as triglycerides.

In another embodiment, the stabilized TAFIa, an inhibitor of TAFIa, or a pharmaceutical composition thereof, can be delivered in a vesicle, in particular a liposome (see Langer, 1990, *Science* 249:1527–1533; Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.).

In yet another embodiment, the stabilized TAFIa, an inhibitor of TAFIa, or a pharmaceutical composition thereof, can be delivered in a controlled release system. In one embodiment, a pump may be used (see Langer, supra; Sefton, 1987, *CRC Crit. Ref. Biomed. Eng.* 14:201; Buchwald et al., 1980, *Surgery* 88:507 Saudek et al., 1989, *N. Engl. J. Med.* 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, 1983, *J. Macromol. Sci. Rev. Macromol. Chem.* 23:61; see also Levy et al., 1985, *Science* 228:190; During et all., 1989, *Ann. Neurol.* 25:351; Howard et al., 1989, *J Neurosurg.* 71:105). Other controlled-release systems discussed in the review by Langer, 1990, *Science* 249:1527–1533) may be used.

5.2.5 Dosages

The amount of the stabilized TAFIa, inhibitor of TAFIa, or pharmaceutical composition thereof which will be effective in the treatment, prevention or management of a hemorrhagic or thrombotic disease or disorder or other disease or disorder that can be treated, prevented or managed by administration of a TAFIa modulator can be determined by standard research techniques. For example, the dosage that will be effective in the treatment, prevention or management of a hemorrhagic or thrombotic disease or disorder can be determined by administering the stabilized TAFIa, inhibitor of TAFIa, or pharmaceutical composition thereof to an animal model such as, e.g., the animal models disclosed herein or known to those skilled in the art. In addition, in vitro assays may optionally be employed to help identify optimal dosage ranges. Selection of the preferred effective dose can be determined via clinical trials.

The precise dose to be employed will also depend on the route of administration, and the seriousness of the hemorrhagic or thrombotic disease or disorder, and should be decided according to the judgment of the practitioner and each patient's circumstances. Effective doses may be extrapolated from dose-response curves derived from in vitro or animal model test systems.

Examples of hemorrhagic animal models include, but are not limited to, those in rats (Sumii, T. and Lo, E. H., *Stroke* 33:831–6 (2002)), rabbits (Zhao, et al., *Brain Res.* 902:30–9 (2001)), dogs (Morales, D., *Circulation* 100:226–9 (1999)), and baboons (Kruithof, E. K., et. al., *Thromb. Haemost.* 77:905–10 (1997)), each of which is incorporated by reference in its entirety herein. Examples of thrombotic animal models include, but are not limited to those in rats (Ravanat, C., et. al., *Thromb. Haemost.* 83:327–33 (2000)), rabbits (Zhao, et al., *Brain Res.* 902:30–9 (2001)), dogs (Bernat A., et. al., *J. Cardiovasc. Pharmacol.* 33:897–904 (1999)), and baboons (Kruithof, E. K., et. al., *Thromb. Haemost.* 77:905–10 (1997)) each of which is incorporated by reference in its entirety herein.

5.3 Diagnostic Assays

5.3.1 Chromogenic Assay

The chromogenic assay according to the present invention is an assay that utilizes stabilized TAFIa as a standard to determine the carboxypeptidase activity of a sample. The assay comprises a carboxypeptidase cleavable substrate wherein the cleavage product is chromogenically detectable.

In a preferred embodiment, the chromogenic assay measures the carboxypeptidase activity of TAFIa. The assay may be used to quantify TAFIa carboxypeptidase activity in purified enzymatic systems or biological samples such as plasma. The assay utilizes a specially formulated developer comprising a carboxypeptidase substrate such as hippuryl-L-lysine or the tetrapeptide pro-phe-gly-lys (PFGK); lysine oxidase; horseradish peroxidase (HRP); a chromogenic substrate of HRP, such as O-phenylene diamine (OPD) or TMB; in any appropriate buffer, e.g., 200 mM Tris-HCl, pH 7.4 buffer. The method of measuring carboxypeptidase activity in a chromogenic assay comprises mixing the biological sample to be tested together with the specially formulated developer, incubating the mixture at 37° C. for 30 minutes followed by quenching with 2M $H_2SO_4$. After stopping the enzymatic reaction, the final colored product is read in a spectrophotometer at a wavelength appropriate for the substrate used. In one embodiment, the assay according to the present invention utilizes small volumes of plasma (about 25 µL) or other sample in total reaction volumes of about 250 µL, which makes reading the assay ideal for use with conventional 96-well microtest plate readers. In another embodiment, the assay according to the present invention can also be easily adapted to larger volumes (about 1 mL) of sample material for reading in standard-sized cuvettes in conventional bench-top spectrophotometers. In another embodiment, the assay according to the present invention can be easily adapted to smaller volumes (less than 25 µL) for reading in high-throughput screening applications. The assay according to the present invention is fairly rapid, with the total assay time being between 30 and 60 minutes. In another embodiment, the biological sample to be tested is incubated with an activation reagent comprising thrombin-thrombomodulin prior to being assayed for carboxypeptidase activity in the chromogenic assay. TAFI in plasma may be in the zymogen form which has low carboxypeptidase activity and must be activated by incubation with an activation reagent comprising thrombin-thrombomodulin. Preferably, the activation reagent formulated as a 30% excess of thrombin in Tris-HCl, pH 7.4. The biological sample is incubated with the activation agent for approximately 10–20 minutes. The activation step is terminated by the addition of activation stop buffer which comprises an inhibitor of thrombin.

5.3.2 Fluorometric Assay

The fluorometric assay according to the present invention is an assay that utilizes stabilized TAFIa as a standard to determine the carboxypeptidase activity of a sample. The assay comprises a carboxypeptidase cleavable substrate wherein the cleavage product is fluorometrically detectable.

The assay may be used to quantify TAFIa carboxypeptidase activity in purified enzymatic systems or biological samples such as plasma. In a preferred embodiment, the fluorometric assay is used to measure endogenous TAFIa activity in plasma and biological fluids without activation of TAFI to TAFIa with thrombin-thrombomodulin. The assay utilizes a specially formulated developer comprising a carboxypeptidase substrate such as hippuryl-L-lysine or the tetrapeptide pro-phe-gly-lys (PFGK); lysine oxidase; horseradish peroxidase (HRP); any fluorescent substrate of HRP (e.g., such as Amplex Red®, QuantaBlu® or AMMB (N-(4-amino-5-methoxy-2-methylphenyl)benzamide); in any appropriate buffer, e.g., 200 mM Tris-HCl, pH 7.4 buffer. The method of measuring carboxypeptidase activity in a chromogenic assay comprises mixing the biological sample to be tested together with the specially formulated developer, incubating the mixture at 37° C. for 30 minutes. The fluorescence is then measured at about 563/605 nm to determine the extent of the reaction. In one embodiment, the assay according to the present invention utilizes small volumes of plasma (about 25 µL) or other sample in total reaction volumes of about 250 µL, which makes reading the assay ideal for use with conventional 96-well microtest plate readers. In another embodiment, the assay according to the present invention can also be easily adapted to larger volumes (about 1 mL) of sample material for reading in standard-sized cuvettes in conventional bench-top fluorometers. In another embodiment, the assay according to the present invention can be easily adapted to smaller volumes (less than 25 µL) for reading in high-throughput screening applications or low volume fluorometers. The assay according to the present invention is fairly rapid, with the total assay time being between 30 and 60 minutes. In another embodiment, the biological sample to be tested is incubated with an activation reagent comprising thrombin-thrombomodulin prior to being assayed for carboxypeptidase activity in the chromogenic assay. TAFI in plasma may be in the zymogen form which has low carboxypeptidase activity and must be activated by incubation with an activation reagent comprising thrombin-thrombomodulin. Preferably, the activation reagent formulated as a 30% excess of thrombin in Tris-HCl, pH 7.4. The biological sample is incubated with the activation agent for approximately 10–20 minutes. The activation step is terminated by the addition of activation stop buffer which comprises an inhibitor of thrombin.

In certain embodiments, the fluorometric assay provides increased sensitivity which allows for the carboxypeptidase activity of biological samples to be measured without prior activation with thrombin-thrombomodulin. In a preferred embodiment, the fluoresent assay as a lower limit of detection of TAFIa in the test sample of 0.1 µg/mL. In a more preferred embodiment, the fluoresent assay has a lower limit of detection of TAFIa in the test sample of 0.02 µg/mL. In a more preferred embodiment, the fluoresent assay has a lower limit of detection of TAFIa in the test sample of 0.01 µg/mL. In a more preferred embodiment, the fluoresent assay has a lower limit of detection of TAFIa in the test sample of 0.002 µg/mL.

5.4 Kits

In one embodiment the invention provides a pharmaceutical pack or kit comprising one or more containers filled with stabilized TAFIa, an inhibitor of TAFIa or pharmaceutical composition thereof, useful in treating, preventing or managing hemorrhagic or thrombotic diseases or disorders. In certain embodiments, the pharmaceutical pack or kit further comprises another therapeutic or prophylactic agent useful in treating, preventing or managing hemorrhagic or thrombotic diseases or disorders. In certain other embodiments, the pharmaceutical pack or kit further comprises another therapeutic or prophylactic agent which is not useful in treating, preventing or managing hemorrhagic or thrombotic diseases or disorders.

In another embodiment invention also provides a pharmaceutical pack or kit comprising one or more containers with stabilized TAFIa, which pack or kit is useful in measuring carboxypeptidase activity of a purified enzyme sample or biological samples such as plasma.

In a preferred embodiment, the kit is useful in measuring TAFIa activity in a purified enzyme sample or a biological sample. In one embodiment, the kit comprises a stabilized TAFIa standard, a buffer comprised of 15% DMSO in 200 mM Tris-HCl (pH 7.4), the tetrapeptide pro-phe-gly-lys (PFGK), a developer and an activation reagent. In another emobodiment, the developer further comprises a chromogenic horseradish peroxidase (HRP) substrate such as, but not limited to, O-phenylene diamine (OPD). In another embodiment, the developer further comprises a fluoresent horseradish peroxidase (HRP) substrate such as, but not limited to, Amplex Red®.

The invention further provides a pack or kit containing one or more buffers, substrates or developers, in one or more containers. Optionally associated with such container(s) can be a notice in the form prescribed by a governmental agency regulating the manufacture, use or sale of pharmaceuticals or biological products, which notice reflects approval by the agency of manufacture, use or sale for human administration. Further optionally associated with such container(s) can be instructions for use.

5.5 Inhibitors of TAFIa

The invention also encompasses a method of treating, preventing or managing a thrombotic disease or disorder comprising administering an inhibitor of TAFIa. In one embodiment, the inhibitor of TAFIa is a peptide. In another embodiment, the inhibitor of TAFIa is a small organic compound (i.e., MW<1000 g/mol). In another embodiment, the inhibitor of TAFIa is a peptide or amino acid linked to a small organic compound. In a preferred embodiment, the inhibitor of TAFIa is captopril, captopril-phe, pro-phe-argininic acid, pro-trp-argininic acid, pro-tyr-argininic acid, pro-phe, pro-trp, pro-tyr, pro-phe-glyargininic acid or argininic acid. Such inhibitors are useful as procoagulants and in the methods as disclosed herein. These inhibitors can be formulated in pharmaceutical compositions as described in section 5.2.3, supra, and administered by the methods described in section 5.2.4, supra.

6. EXAMPLES

The following examples are offered by way of illustration, not limitation.

6.1 Activation of Stabilized TAFIa

TAFI (100 µg in 100 µL) (wild-type or mutant) is mixed with thrombin-thrombomodulin (300 µg in 0.3 mL) in 600 µL of HBS buffer. The activation is initiated with the addition of the 5 µL of the human thrombin (83 U/µL). The activation is done at room temperature for 50 minutes. A thrombin inhibitor (e.g., PPACK, ThromStop, etc.) is added to stop the reaction. The mixture containing TAFIa is diluted with 9.5 mL of 20 mM Tris-HCl, pH 7.4.

6.2 Purification of Stabilized TAFIa by PTCI-Sepharose

The potato tuber carboxypeptidase inhibitor (PTCI)-Sepharose was extensively washed with 20 mM Tris-HCl, pH 7.4. The TAFIa was loaded (0.5 mL/min) and the column was washed with 10 column volumes with 20 mM Tris-HCl, pH 7.4. TAFIa was eluted with 0.5 M NaCl/1 mM amino caproic acid in 20 mM Tris-HCl pH 7.4. The fractions were stored at 0° C. and assayed using the TAFI chromogenic assay for determination of carboxypeptidase activity.

6.3 Effects of Stabilized TAFIa on Fibrinolysis

Figure 4:
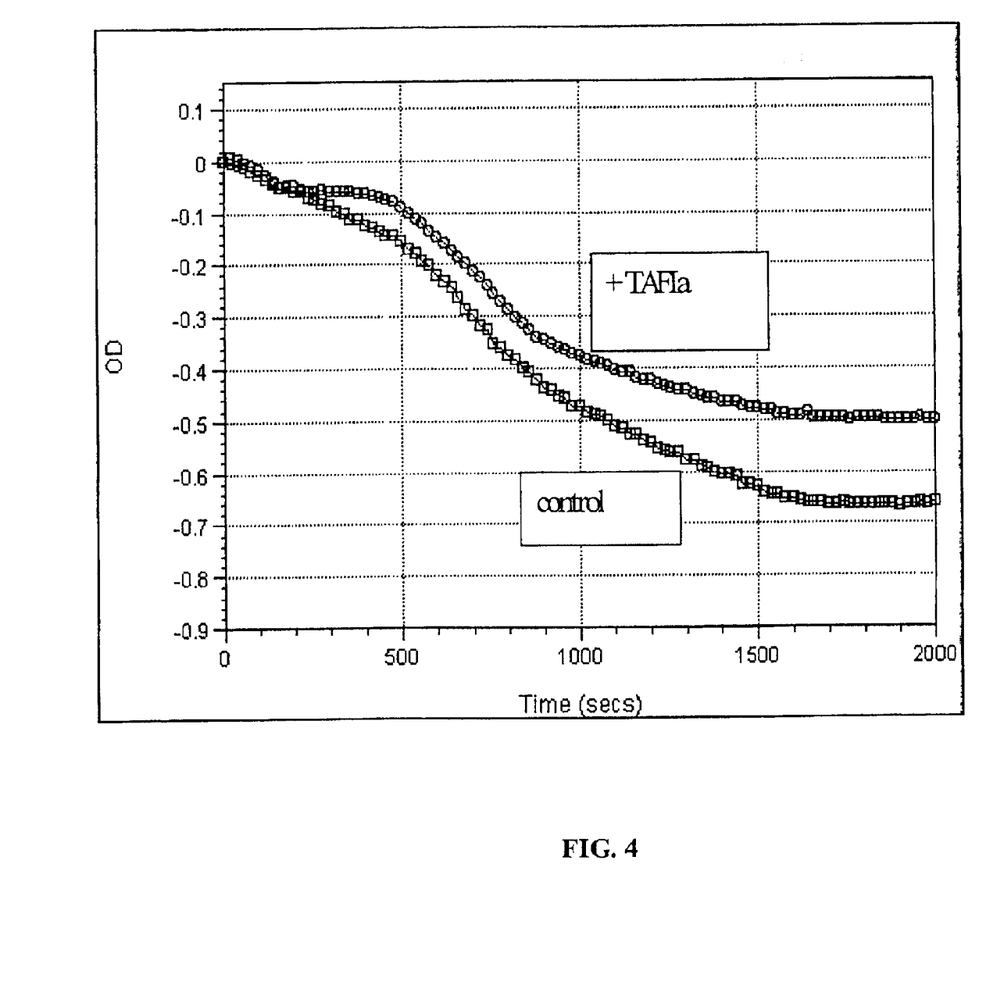
FIG. 4 illustrates the effect of purified TAFIa on fibrinolysis.

Human plasma was activated by addition of thrombin/thrombomodulin complex in the presence and the absence of purified TAFIa (5 µg/mL). After the formation of the clot, t-PA was added (4 ng in 1 µL) and fibrinolysis was monitored spectrophotometrically for 4 hr. FIG. 4 shows that the addition of purified TAFIa prolonged clot lysis time relative to control.

6.4 Chromogenic Assay Protocol Using TAFI Chromogenic Assay Kit

This example describes the assay procedure to determine TAFIa activity in a plasma sample using a 96-well microtest plate. If the plasma sample is frozen, it should be thawed at 37° C. for 15 minutes before testing. Assay buffer, such as 200 mM Tris-HCl, pH 7.4 (480 µL), is added to plasma (20 µL) in a 1.5 mL centrifuge tube followed by vortexing to give a 1:25 dilution. The TAFIa standard should be reconstituted immediately before use in the assay by the addition of 500 µL of cold (2–8° C.) filtered (0.22 µm filter) deionized $H_2O$ to vial containing the TAFIa standard followed by gently vortexing.

TAFIa in the plasma sample is activated by adding the following to a microtest well: assay buffer, such as 200 mM Tris-HCl, pH 7.4 (90 µL), 1:25 dilution of plasma (25 µL), TAFI activation enhancer reagent (comprising $CaCl_2$ and pro-gly-arg-pro) (10 µL) and TAFI activation reagent (thrombin-thrombomodulin) (15 µL) followed by incubation at room temperature on a shaker for 20 minutes. The activation reaction is quenched by the addition of the activation stop reagent (a thrombin inhibitor) (10 µL).

An unactivated plasma sample for use as a control is prepared by adding the following to a microtest well: assay buffer, such as 200 mM Tris-HCl, pH 7.4 (115 µL) and 1:25 dilution of plasma (25 µL) followed by incubation at room temperature on a shaker for 20 minutes. This is followed by the addition of the activation stop reagent (a thrombin inhibitor) (10 µL).

A standard curve to be used in determining the level of TAFIa activity in the plasma sample is prepared by making five serial dilutions of TAFIa standard as follows: add 50 μL of TAFIa standard and 250 μL of assay buffer, such as 200 mM Tris-HCl, pH 7.4, to the top well in a column of the 96-well microtest plate followed by mixing; add 150 μL of assay buffer, such as 200 mM Tris-HCl, pH 7.4, to the four wells directly beneath the top well; remove 150 μL from the top well and place into the well directly beneath it followed by mixing; repeat with the remaining three wells.

The assay is initiated by the addition of TAFI developer (50 μL) to wells containing activated plasma, unactivated plasma and the TAFIa standards followed by incubation at 37° C. with shaking for 30 minutes. A yellow color will appear and increase with intensity over time (the kinetics can be measured by monitoring the development of the yellow color at 420 nm). The reaction is quenched by the addition of 50 μL of 2M $H_2SO_4$ to each well. The absorbance of each well is measured at 490 nm to determine the extent of the reaction. The amount of TAFIa present in the plasma samples is determined by comparison with the values obtained from the standard curve.

6.5 Fluorometric Assay Protocol Using TAFI Fluorometric Assay Kit

This example describes the assay procedure to determine TAFIa activity in a plasma sample using a 96-well microtest plate. If the plasma sample is frozen, it should be thawed at 37° C. for 15 minutes before testing. Assay buffer, such as 200 mM Tris-HCl, pH 7.4 (480 μL), is added to plasma (20 μL) in a 1.5 mL centrifuge tube followed by vortexing to give a 1:25 dilution. The TAFIa standard should be reconstituted immediately before use in the assay by the addition of 500 μL of cold (2–8° C.) filtered (0.22 μm filter) deionized $H_2O$ to vial containing the TAFIa standard followed by gently vortexing.

TAFIa in the plasma sample is optionally activated by adding the following to a microtest well: assay buffer, such as 200 mM Tris-HCl, pH 7.4 (90 μL), 1:25 dilution of plasma (25 μL), TAFI activation enhancer reagent (comprising $CaCl_2$ and pro-gly-arg-pro) (10 μL) and TAFI activation reagent (thrombin-thrombomodulin) (15 μL) followed by incubation at room temperature on a shaker for 20 minutes. The activation reaction is quenched by the addition of the activation stop reagent (a thrombin inhibitor) (10 μL).

An unactivated plasma sample for use as a control is prepared by adding the following to a microtest well: assay buffer, such as 200 mM Tris-HCl, pH 7.4 (115 μL) and 1:25 dilution of plasma (25 μL) followed by incubation at room temperature on a shaker for 20 minutes. This is followed by the addition of the activation stop reagent (a thrombin inhibitor) (10 μL).

A standard curve to be used in determining the level of TAFIa activity in the plasma sample is prepared by making five serial dilutions of TAFIa standard as follows: add 50 μL of TAFIa standard and 250 μL of assay buffer, such as 200 mM Tris-HCl, pH 7.4, to the top well in a column of the 96-well microtest plate followed by mixing; add 150 μL of Assay buffer, such as 200 mM Tris-HCl, pH 7.4, to the four wells directly beneath the top well; remove 150 μL from the top well and place into the well directly beneath it followed by mixing; repeat with the remaining three wells.

The assay is initiated by the addition of TAFI developer (50 μL) to wells containing activated plasma, unactivated plasma and the TAFIa standards followed by incubation at 37° C. with shaking for 30 minutes. The reaction is quenched with a sodium azide solution and the fluorescence of each well is measured at about 563/605 nm to determine the extent of the reaction. The amount of TAFIa present in the plasma samples is determined by comparison with the values obtained from the standard curve.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A kit comprising as components purified, stabilized TAFIa, a developer, an activation reagent, and a buffer comprising 15% DMSO, 200 mM Tris-HCl at pH 7.4, each said component being in a separate container, and instructions for use of said kit.

2. The kit of claim 1, wherein the developer comprises a carboxypeptidase cleavable substrate.

3. The kit of claim 2, wherein the carboxypeptidase cleavable substrate is pro-phe-gly-lys.

4. The kit of claim 2, wherein the carboxypeptidase cleavable substrate is hippuryl-L-lysine.

5. The kit of claim 2, wherein the carboxypeptidase cleavable substrate is hippuryl-L-arginine.

6. The kit of claim 2, wherein the developer comprises lysine oxidase and horseradish peroxidase.

7. The kit of claim 2, wherein the developer contains a chromogenic horseradish peroxidase substrate.

8. The kit of claim 2, wherein the developer contains a fluorogenic horseradish peroxidase substrate.

9. A kit comprising as components purified, stabilized TAFIa, a developer, and an activation reagent, each said component being in a separate container, and instructions for use of said kit, wherein at least one of the components is in a buffer comprising 15% DMSO, 200 mM Tris-HCl at pH 7.4.

10. The kit of claim 9, wherein the developer comprises a carboxypeptidase cleavable substrate.

11. The kit of claim 10, wherein the carboxypeptidase cleavable substrate is pro-phe-gly-lys.

12. The kit of claim 10, wherein the carboxypeptidase cleavable substrate is hippuryl-L-lysine.

13. The kit of claim 10, wherein the carboxypeptidase cleavable substrate is hippuryl-L-arginine.

14. The kit of claim 10, wherein the developer comprises lysine oxidase and horseradish peroxidase.

15. The kit of claim 10, wherein the developer contains a chromogenic horseradish peroxidase substrate.

16. The kit of claim 10, wherein the developer contains a fluorogenic horseradish peroxidase substrate.

* * * * *